United States Patent [19]

Naser

[11] Patent Number: 5,935,780
[45] Date of Patent: *Aug. 10, 1999

[54] METHOD FOR THE QUALITATIVE OR/AND QUANTITATIVE DETECTION OF AN ANALYTE

[75] Inventor: Werner Naser, Weilheim, Germany

[73] Assignee: Boehringer Mannheim GmbH, Mannheim, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/531,838

[22] Filed: Sep. 21, 1995

[30] Foreign Application Priority Data

Sep. 23, 1994 [DE] Germany ............................. 44 34 093

[51] Int. Cl.⁶ .................................................. G01N 33/533
[52] U.S. Cl. .................................. 435/6; 422/56; 422/60; 435/7.1; 435/7.2; 435/7.9; 435/7.93; 435/7.94; 435/7.95; 435/287.7; 435/287.8; 435/287.9; 435/962; 435/969; 436/518; 436/529; 436/540; 436/541; 436/823; 436/825
[58] Field of Search ............................... 422/56–60, 100; 435/6, 7.1, 7.2, 962, 7.5, 969, 7.9, 7.93, 7.94, 7.95, 287.7, 287.8, 287.9; 436/518, 529, 540, 541, 823, 825

[56] References Cited

U.S. PATENT DOCUMENTS

| | | |
|---|---|---|
| 4,228,237 | 10/1980 | Hevey et al. . |
| 4,243,655 | 1/1981 | Gunther . |
| 4,243,749 | 1/1981 | Sadeh et al. . |
| 4,298,685 | 11/1981 | Parikh et al. . |
| 4,468,470 | 8/1984 | Aalberse . |
| 4,490,473 | 12/1984 | Brunhouse . |
| 4,656,252 | 4/1987 | Giese . |
| 4,945,042 | 7/1990 | Geiger et al. . |
| 5,268,306 | 12/1993 | Berger et al. . |
| 5,277,589 | 1/1994 | Schmitt et al. . |
| 5,378,638 | 1/1995 | Deeg et al. . |
| 5,441,869 | 8/1995 | Dessauer et al. . |

FOREIGN PATENT DOCUMENTS 0 265 244  4/1988  European Pat. Off. .

OTHER PUBLICATIONS

Wilchek et al., Immunology Today, vol. 5, No. 2, 1984.
International Publication No. WO 94/10573 published May 11, 1949.
International Publication No. WO 91/12336 published Aug. 22, 1991.

Primary Examiner—James C. Housel
Assistant Examiner—Bao-Thuy L. Nguyen
Attorney, Agent, or Firm—Nikaido Marmelstein Murray & Oram, LLP.

[57] ABSTRACT

For the qualitative or/and quantitative detection of a substance to be determined in a test sample with the aid of an immunoassay or nucleic acid hybridization assay the following components are used:

a) a capture reagent which enables a specific detection of the substance to be determined by means of two different binding sites 1) if desired together with further test components and 2) is bound or is capable of binding to an active solid phase via a specific binding pair one partner of which is linked to the capture reagent and the second partner of which is coupled to an active solid phase b) an active solid phase and c) an inactive solid phase which substantially corresponds to the active solid phase but to which the capture reagent cannot bind,
wherein the test sample is either firstly brought into contact with the inactive solid phase alone and only later with the active solid phase, or is simultaneously brought into contact with the active and inactive solid phase during which the capture reagent and if desired further test components are either present from the start or are only added later and the substance to be determined is detected.

37 Claims, No Drawings

METHOD FOR THE QUALITATIVE OR/AND QUANTITATIVE DETECTION OF AN ANALYTE

DESCRIPTION

The present invention concerns a method for the qualitative or/and quantitative detection of a substance to be determined in a test sample with the aid of an immunoassay or nucleic acid hybridization assay, an inactivated solid phase for use in such an assay as well as the use of this inactivated solid phase for eliminating interference in immunoassays or nucleic acid hybridization assays by capturing components which bind unspecifically in a test sample to be analysed. Finally the invention also concerns a test kit containing the usual components of an immunoassay or nucleic acid hybridization assay as well as an inactivated solid phase according to the invention.

Nowadays immunoassays and nucleic acid hybridization assays serve as a rapid and simple test for substances for example in the area of diagnostics. They can be used to rapidly and reliably detect the presence of endogenous or exogenous substances in biological samples. Immunoassays and nucleic acid hybridization assays are based on the principle that a substance to be detected specifically binds to another substance and, if the assay is suitably designed, the presence of the substance to be detected can be determined with the aid of this other substance. The capability of the substance to be determined to specifically bind to one or several further substances is thus utilized to enable detection. However, in this process side reactions can also occur such as undesired interactions and unspecific binding reactions. In particular when using a solid phase on which substances that bind specifically are immobilized or can be immobilized, the problem occurs that additional substances are often present in the test sample which also bind to this solid phase and thus result in false positive signals. This can increase the background signal and a larger scatter of the signals can occur thus resulting in a decreased sensitivity and specificity of the respective test.

In order to avoid interactions with non-specific factors it is for example proposed in the European Patent Application EP 0 163 312 that ultrafine particles should be added to the reagents of the immunoassay which have a maximum average size of 0.2 $\mu$m and are formed in such a way that they are capable of binding to the substance that causes the unspecific reaction and of capturing it.

However, it is necessary to specially prepare these ultrafine particles for this and it must also be known which unspecific factors are actually present in the sample.

However, it would be an advantage if a method could be provided which generally and universally eliminates interferences in immunoassays or nucleic acid hybridization assays even without knowing the interfering substances that are actually present. It was therefore the object of the present invention to provide an appropriate method. This object is achieved according to the invention by a method for the qualitative or/and quantitative detection of a substance to be determined in a test sample with the aid of an immunoassay or nucleic acid hybridization assay in which the following components are used:

a) a capture reagent which enables a specific detection of the substance to be determined by means of two different binding sites 1) if desired together with further test components and 2) is bound or is capable of binding to an active solid phase via a specific binding pair one partner of which is linked to the capture reagent and the second partner of which is coupled to an active solid phase, b) an active solid phase and c) an inactivated solid phase which substantially corresponds to the active solid phase but to which the capture reagent cannot bind wherein the test sample is either firstly brought into contact with the inactivated solid phase alone and only later with the active solid phase or is simultaneously brought into contact with the active and inactivated solid phase during which the capture reagent and if desired further test components are either present from the start or are only added later and the substance to be determined is detected.

The capture reagent according to the invention is designed in such a way that it has two types of binding sites. It can be coupled to one partner of a specific binding pair by means of one type of binding site. Coupling to several partners of binding pairs is also possible. Furthermore the capture reagent according to the invention has a further type of binding site that enables a specific detection of the substance to be determined. These binding sites are preferably capable of specific binding to the substance to be determined or to a complex of the substance to be determined and further test components. A capture reagent can also have several binding sites of this kind, antibodies for example have two epitopes with specific binding sites.

In the method according to the invention substances are preferably used as the capture reagent which are capable of specific binding to the substance to be determined. If the substance to be determined is an antibody then a corresponding antigen, hapten or even a second antibody directed against the antibody to be determined or a fragment thereof is used as the capture reagent. If in contrast the substance to be determined is an antigen, an antibody or antibody fragment is used as the capture reagent. If the substance to be determined is a nucleic acid, a nucleic acid oligomer or nucleic acid polymer or a nucleic acid analogue is used as the capture reagent. In this case it is preferable to use a peptidic nucleic acid as the nucleic acid analogue.

In this connection the capture reagent is designed according to the invention in such a way that it can be bound to a solid phase via a specific binding pair using a site of the molecule that does not interfere with the binding of the substance to be determined or it can be present already bound to the solid phase. This binding can either be carried out directly via the binding pair. However, the capture reagent can also be coupled to the solid phase by means of a binding system composed of more than two components that are capable of binding to one another. One partner of the specific binding pair is always linked to the capture reagent and a second partner of the specific binding pair is coupled to a solid phase. This coupling can in turn be achieved by all methods known to a person skilled in the art and coupling of the capture reagent to the solid phase via the specific binding pair can take place before carrying out the immunoassay or not until during the immunoassay in which case the capture reagent is only added to the other components of the immunoassay at a later time.

In a preferred embodiment of the invention biotin/avidin, biotin/streptavidin, antigen/antibody, hapten/antibody pairs or fragments thereof capable of specific binding to one another are used as the specific binding pair. In a particularly preferred embodiment of the invention biotin/avidin or biotin/ streptavidin is used as the specific binding pair.

The substance to be determined is detected according to the invention by means of a detection reagent which together with the capture reagent enables a specific detection of the substance to be determined and carries an indirect or direct label. Using directly labelled detection reagents the detection is carried out either in that the detection reagent binds to the substance to be determined and a detectable sandwich complex that carries the label is formed or binds to the capture reagent in competition with the substance to be determined and forms a detection reagent-capture reagent complex that carries the label. Detection reagents with an indirect label are composed of several components in which the component that binds to the substance to be determined or to the capture reagent is unlabelled and is capable of binding to a further component that carries the label.

Suitable labels are known to a person skilled in the art. Radioactive labels, chemiluminescent labels, fluorescent labels or electrochemiluminescent labels, dyed particles such as e.g. metal sol particles or dyed or undyed latex are preferably used for this. The label can also generate an indirect signal such as for example in the case of enzyme labels using enzymes such as peroxidase, β-galactosidase or alkaline phosphatase. The label can preferably be determined according to the invention on the active solid phase or/and in the sample supernatant.

According to the invention all known methods of detection can be used to detect the substance to be determined. The test can for example be carried out as a so-called displacement method or as a sandwich method. In the displacement method which is preferred according to the invention a labelled detection reagent is used which has the same or a similar binding site as the substance to be determined and thus competes with the substance to be determined. If for example the substance to be determined is an antibody, then an appropriate antigen as capture reagent and a labelled antibody are added in order to detect this antibody in the displacement method in which case the labelled antibody has the same or similar binding specificity as the antibody to be determined. The antigen can be directly linked or capable of binding to the solid phase via a specific binding pair the first partner of which is linked to the antigen and the second partner of which is coupled to the active solid phase. The antigen can also become or be indirectly immobilized on the solid phase via a second antibody which is capable of binding to or is bound to the solid phase. Like the labelled antibody this second antibody can also have the same or a similar specificity as the antibody to be determined. The sample antibody competes with the labelled antibody and if desired with the second antibody for binding to the antigen.

If the substance to be determined is an antigen then an immunologically competing analogue of the antigen to be determined is preferably used for detection in the displacement method. This is for example the same antigen or/and an antigen with similar binding specificity. If it is a nucleic acid, a nucleic acid oligomer or nucleic acid polymer or nucleic acid analogue and particularly preferably a peptidic nucleic acid is preferably used as the detection reagent.

According to the invention the substance to be determined is especially preferably detected in a sandwich method. In this case the detection reagent is capable of specific binding to the substance to be determined. If the substance to be determined is in turn an antibody, it is possible to use an antigen, a hapten or a second antibody directed against the first antibody or an antibody fragment as the detection reagent. If on the other hand the substance to be determined is an antigen, then an antibody or antibody fragment is used as the detection reagent which binds to an epitope of the antigen which is different from that of the capture reagent. If the substance to be determined is a nucleic acid such as for example an oligonucleotide or a section of DNA or RNA, it is expedient to use a nucleic acid oligomer or nucleic acid polymer or an analogous structure as the capture reagent with a sequence region that is complementary to the substance to be determined.

Structures with modified nucleobases, sugars or/and internucleotidic bonds can be used as nucleic acid analogues. Peptidic nucleic acids/PNA are particularly well suited as nucleotide analogues. Suitable capture and detection reagents for such immunoassays and nucleic acid hybridization assays and in particular "sandwich assays" are in general known to a person skilled in the art and do not have to be definitively elucidated here.

In the sandwich detection method that is preferred according to the invention a complex is formed from a substance to be determined, a capture reagent which mediates binding to a solid phase and a detection reagent that carries a label and thus enables detection of the presence of the substance to be determined. The order in which the individual test components are added is uncritical in the test procedure.

An active solid phase is used in addition to the capture reagent and if necessary the detection reagent for the method according to the invention. This active solid phase either contains the capture reagent already in a bound form or it is designed in such a way that the capture reagent can bind to the solid phase. The term "active" solid phase should make clear that this solid phase enables the detection of the substance to be determined by means of the capture reagent. The capture reagent preferably enables the detection reagent to bind to the active solid phase by means of which unbound components are separated and the substance to be determined can be detected. However, in contrast to the previously known immunoassays and nucleic acid hybridization assays the method according to the invention uses an additional inactive solid phase which, although substantially corresponding to the active solid phase, is modified in such a way that the capture reagent cannot bind thereto. However, unspecific binding that is not mediated by the capture reagent or by its specific binding to the solid phase can occur on this inactive solid phase. The use of this inactive solid phase which can either be preincubated with the test sample alone but can also be used in combination with one or several or ultimately with all other components of the immunoassay enables the interception of unspecific binding and thus prevents bridging through unspecific binding of whatever kind from occurring on the active solid phase and thus prevents binding of a detection reagent to the active solid phase and consequent generation of a false positive signal.

The test sample is preferably firstly incubated with the inactive solid phase alone. In this process all unspecific substances capable of binding to the solid phase can react after which the test sample can be separated from the inactive solid phase and then incubated in an arbitrary sequence or combination with the active solid phase and the other components such as capture reagent and if desired detection reagent and additional test components and the substance to be determined can be detected via the signal of the label.

In another preferred embodiment the inactive and the active solid phase are simultaneously contacted with the test sample and if desired also with the other components of the immunoassay or nucleic acid hybridization assay which at least considerably reduces the background and interfering signals by also binding unspecific substances to the inactive solid phase.

Within the scope of the invention all solid phases that can be used for immunoassays can be used as solid phases. Plastic tubes, microtitre plates, glass or plastic beads or latex particles are preferably used as the solid phase. It is however, also possible to use test strips made of paper or plastic.

The solid phase can be inactivated in various ways. However, in this process it has to be ensured that the specific binding of the capture reagent to the solid phase cannot take place. In a particularly preferred embodiment of the invention in which biotin/streptavidin or biotin/avidin is used as the specific binding pair and of which avidin or streptavidin are present bound to the solid phase, avidin or streptavidin are inactivated in the production of the inactive solid phase by saturation with biotin or a biotin derivative. Moreover avidin or streptavidin that are bound to the solid phase or are to be bound thereto, can preferably be inactivated by covalent modification of the active centre. Such a covalent modification is preferably achieved by derivatizing at least one amino acid of the active centre or by covalently coupling biotin to the active centre. In this case covalent coupling can preferably be achieved by coupling biotin that can be photoactivated such as for example biotin-DADOO-AB to avidin or streptavidin.

It is however, also possible—and this is also especially preferred within the scope of the invention—to use avidin or steptavidin that has been produced by genetic engineering to produce the inactive solid phase in which binding of biotin is prevented by modifying the active centre by means of genetic engineering such as by substituting, deleting or inserting individual or several amino acids.

The use of fragments of avidin or streptavidin seems possible provided that the solid phase coupled thereto is still capable of capturing sufficient unspecific binding. This can be ascertained by simple preliminary tests.

Aqueous samples can generally be used as the test sample, body fluids and in particular blood, blood plasma, serum, saliva, tissue fluids such as for example tissue fluid obtained through the skin with the aid of skin patches, liquor or urine being used in diagnostics. The test sample is therefore preferably a body fluid.

In the method according to the invention it is preferred in the case that the substance to be determined is an antigen, to use antibodies or antibody fragments as the capture reagent and if desired detection reagent. Conversely if the substance to be detected is an antibody, antigens or/and haptens are used as capture or/and detection reagents and one or both reagents can be an antigen or/and a hapten and the other reagent is a second antibody directed against the antibody to be determined. If the substance to be determined is a nucleic acid such as for example an oligonucleotide or a section of DNA or RNA, it is expedient to use a nucleic acid oligomer or nucleic acid polymer or a nucleic acid analogue and especially preferably a peptidic nucleic acid.

The method according to the invention can be carried out in such a way that all components including the solid phase are firstly introduced into the reaction vessel. In this case it is preferable to use modified glass or plastic beads as the solid phases. However, the immunoassay can also be carried out by using the reaction vessel as one of the two solid phases and glass or plastic beads as the other one of the two solid phases. Solid phases in the form of a test strip can also be used in which either both solid phases can be designed as test strips or the reaction vessel can again represent one of the two solid phases.

Streptavidin or avidin as one partner of a specific binding system is coupled to the solid phase by means of thermo-bovine-serum-albumin (TBSA) in an especially preferred embodiment of the invention.

In an additional preferred embodiment of the invention microtitre plates are in each case used as the solid phases. A plate in this case also stands for other shapes e.g. 8 and 16-well strips. In this case several different immunoassays or nucleic acid hybridization assays can be carried out simultaneously. For this the test sample is firstly brought into contact with a microtitre plate designed as an inactivated solid phase if desired in the presence of a detection or/and capture reagent, the samples being introduced into the wells. After a preincubation period in which unspecific binding with the inactivated solid phase can take place various parallel samples are then transferred without delay by pipette, preferably a multi-channel pipette into a further microtitre plate that is designed as an active solid phase.

Pipetting with the multi-channel pipette has the advantage that pipetting into the wells containing active solid phase occurs simultaneously and thus an increased test precision can be achieved, possibly at the same time with an overall shorter test period.

In addition the present invention concerns an inactive solid phase for use in immunoassays or nucleic acid hybridization assays which is characterized in that it corresponds to a solid phase used in an immunoassay or nucleic acid hybridization assay but is modified in such a way that no binding to a capture reagent can take place. A capture reagent is in turn understood as a reagent capable of specific binding to a substance to be detected in an immunoassay or nucleic acid hybridization assay, which can mediate wall-binding due to its ability to bind to a solid phase.

The inactivated solid phase is preferably a plastic tube, a microtitre plate, glass or plastic beads or latex particles.

This inactivated solid phase preferably has binding pairs biotin/streptavidin, biotin/avidin, antigen/ antibody, hapten/ antihapten antibody or fragments that are each capable of binding to one another as the partner. These partners of a binding pair are linked to the inactivated solid phase by known methods such as for example by adsorptive coating. In this connection it is especially preferred that avidin or streptavidin is bound to the solid phase as a partner of the binding pair wherein coupling is particularly preferably achieved by means of coating with thermo-BSA (TBSA). The inactive solid phase according to the invention is preferably inactivated by saturation of avidin or streptavidin with biotin or a biotin derivative, by covalently modifying the active centre of avidin or streptavidin whereby it is particularly preferable to covalently modify by derivatizing at least one amino acid of the active centre or by covalently coupling biotin to the active centre. An additional possibility of inactivating the inactive solid phase according to the invention is to covalently couple biotin to the active centre by using biotin that can be photoactivated for example biotin-DADOO-AB and subsequently photoactivating. The use of such fragments of avidin or streptavidin to which biotin can no longer specifically bind on the solid phase and production of an inactivated solid phase in this manner is possible within the scope of the invention. Finally it is particularly preferred within the scope of the invention to inactivate the active centre of avidin or streptavidin by a modification using genetic engineering such as the substitution, deletion or insertion of individual or several amino acid residues.

Furthermore the present invention concerns the use of an inactive solid phase according to the invention to eliminate interference in immunoassays or nucleic acid hybridization assays by capturing components that bind unspecifically in a sample to be analysed. The method according to the invention or the use of the inactivated solid phase according to the invention in an immunoassay or nucleic acid hybridization assay enables interferences by components that bind unspecifically to be brought under control in a simple and cost-effective manner and afterwards allows the immunoassay to be performed free from interference. In this method false positive results are avoided in the same way as too wider scatter of test results which also impairs the sensitivity and specificity of the respective test.

In addition the present invention concerns a test kit for immunoassays or nucleic acid hybridization assays for the qualitative or/and quantitative detection of a substance in a test sample wherein the test kit contains the usual components for an immunoassay or nucleic acid hybridization assay and an inactivated solid phase which substantially corresponds to an active solid phase used in an immunoassay or nucleic acid hybridization assay but to which the capture reagent cannot bind. The test kit preferably contains the following components:

a) a capture reagent which enables a specific detection of the substance to be determined by means of two different binding sites 1) if desired together with further test components and 2) is bound or capable of binding to an active solid phase via a specific binding pair one partner of which is linked to the capture reagent and the second partner of which is coupled to an active solid phase,
b) a detection reagent
c) an active solid phase and
d) an inactivated solid phase according to the invention.

In addition the present invention concerns a method for preventing interference by unspecific binding to the solid phase in an immunoassay using the following components
a) a capture reagent which enables a specific detection of the substance to be determined by means of two different binding sites 1) if desired together with further test components and 2) is bound or capable of binding to an active solid phase via a specific binding pair one partner of which is linked to the capture reagent and the second partner of which is coupled to an active solid phase
b) at least two active solid phases which is characterized in that the test sample is incubated in the presence of a first active solid phase before addition of the capture reagent and if desired of further test components and afterwards the test sample is separated from this first solid phase and then an incubation is carried out in the presence of capture reagent and if desired further test components and of a second solid phase that is substantially identical and the substance to be determined is detected in a suitable manner. This method also enables unspecific interferences caused by binding of substances present in the test sample to the solid phase and thus generation of an unspecific signal to be avoided. Substances that bind unspecifically are captured in advance by preincubation with an active solid phase that corresponds to the solid phase used in the immunoassay wherein the actual immunoassay is not carried out until the solid phase has been separated and subsequent incubation with the components capture reagent, if desired detection reagent and a new uncoated test phase. The substance to be determined cannot yet be bound to the active solid phase during the preincubation since the capture reagent is only added after the subsequent second incubation. It is not absolutely necessary to inactivate the solid phase in this embodiment.

The following example is intended to elucidate the invention in more detail:

EXAMPLE 1

Comparative test procedure for an immunoassay for the determination of anti-GAD antibodies in human serum:
A) Test procedure according to methods previously used:
100 $\mu$l of a solution composed of biotinylated glutamate decarboxylase (GAD) at a concentration of ca. 1 $\mu$g/ml is pipetted into each well of an active streptavidin-coated microtitre plate and incubated for one hour at room temperature. Afterwards the plate is washed three times with a suitable buffer. Human serum is diluted 1+25 in incubation buffer from the Enzymun Test® anti-HIV 1+2 of which 100 $\mu$l is in turn pipetted into the respective wells of the microtitre plate and incubated for one hour at room temperature. The samples are also aspirated after this step and the wells are washed three times. The POD-coupled detection antibody from sheep having binding specificity for human IgG (sheep-(anti-) human POD) is diluted to a concentration of ca. 75 mU/ml in conjugate buffer from the Enzymun-Test® anti-HIV 1+2 and 100 $\mu$l of this diluted solution is added to each well of the microtitre plate and incubated for one hour at room temperature. The liquid is again aspirated, the plate is washed three times as above. The dye ABTS® is dissolved to a concentration of 1 mg/ml in Enzymun-Test® substrate buffer and 100 $\mu$l are pipetted into each well of the microtitre plate and incubated. The absorption is read in a microtitre plate photometer after ca. 30 min. The measuring wavelength is 405 nm and the reference wavelength is 492 nm. The blank is determined from two untreated cuvettes that only contain substrate/dye solution. The results of the GAD determination with eight different sera is shown in Table 1 in the column "without preincubation".

B) Test procedure according to the method of the invention

A solution of biotinylated GAD (ca. 1 $\mu$g/ml) and serum (1:26) is prepared in a suitable buffer as described in 1A) and incubated for one hour in a microtitre plate coated with inactivated streptavidin in an amount of 250 $\mu$l of this solution per well. Two 100 $\mu$l aliquots from each well are pipetted into a well of a plate coated with active streptavidin and again incubated for one hour. Afterwards the solution is removed by pipette, it is washed three times with buffer, incubated with sheep-(anti-)human POD and the colour-forming reaction is carried out according to 1A). The values obtained by the procedure according to the invention can be seen in Table 1 in the column which is denoted "with incubation".

These data clearly show the dramatic reduction of unspecific binding in the procedure according to the invention.

TABLE 1

| Interfering sera | with incubation | without preincubation |
|---|---|---|
| 7478-262 | 15 | 260 |
| -269 | 45 | 468 |
| -272 | 30 | 1669 |
| -289 | 69 | 2208 |
| 7480-203 | 97 | 1343 |
| -210 | 72 | 136 |
| 7463-531 | 0 | 1613 |
| 7478-298 | 182 | 1517 |

I claim:
1. A method for the qualitative or quantitative detection of a substance to be detected in a test sample, the method comprising:
(a) providing an immunoassay or nucleic acid hybridization assay comprising
(1) a first solid phase;
(2) an amount of a capture reagent having a first binding site and a second binding site; and
(3) a second solid phase which is does not specifically bind the capture reagent via the first binding site, wherein the second solid phase is coated with a specific binding pair, wherein the specific binding pair is selected from the group consisting of biotin/ avidin, biotin/streptavidin, antigen/antibody and hapten/antihapten, or fragments thereof which specifically bind to each other;

(b) incubating the test sample, containing an amount of the substance to be detected therein, with the immunoassay or nucleic hybridization assay to (1) directly or indirectly specifically bind at least a portion of the amount of the substance to be detected to either (i) the first solid phase via the second binding site of the capture reagent, wherein the capture reagent directly or indirectly specifically binds to the first solid phase via the first binding site, and binding a labelled detection reagent either to at least a portion of the amount of the substance to be detected or at least a portion of the amount of the capture reagent, and thereafter qualitatively or quantitatively detecting the label as an indication of the presence or the amount of the substance to be detected, or (ii) a labelled detection reagent, and thereafter qualitatively or quantitatively detecting the label as an indication of the presence or the amount of the substance to be detected, and (2) unspecifically bind interfering substances to the second solid phase.

2. The method of claim 1, wherein, in step (b), the test sample is first incubated with the second solid phase and is thereafter incubated with the first solid phase and the capture reagent.

3. The method of claim 1, wherein, in step (b), the test sample is first incubated with the first solid phase and thereafter the capture reagent is contacted with the test sample and the first solid phase.

4. The method of claim 1, wherein, step (b) comprises incubating the test sample with the second solid phase, thereafter incubating the test sample with the first solid phase, and thereafter incubating the test sample with the capture reagent.

5. The method of claim 1, wherein the first solid phase and the second solid phase are each independently selected from the group consisting of plastic tubes, microtitre plates, glass beads, plastic beads and latex particles.

6. The method of claim 1, wherein step (b) comprises incubating the test sample with the second solid phase and the capture reagent to bind at least a portion of the amount of the substance to be detected with the capture reagent to form a capture reagent/substance complex, thereafter separating the second solid phase from the capture reagent/ substance complex, and thereafter incubating the capture reagent/substance complex with the first solid phase.

7. The method of claim 1, wherein the capture reagent binds to the first solid phase via a specific binding pair, wherein the specific binding pair is selected from the group consisting of biotin/avidin, biotin/streptavidin, antigen/ antibody and hapten/anti-hapten, or fragments thereof which specifically bind to each other.

8. The method of claim 1, wherein the capture reagent binds to the first solid phase via a specific binding pair, wherein the specific binding pair is selected from the group consisting of biotin/avidin and biotin/streptavidin, wherein avidin or steptavidin is bound to the first solid phase.

9. The method of claim 8, wherein the avidin or steptavidin is bound to the first solid phase via thermo-bovineserum-albumin.

10. The method of claim 1, wherein the test sample is a body fluid sample.

11. The method of claim 10, wherein the body fluid sample is selected from the group consisting of blood, blood plasma, serum, saliva, tissue fluid, liquor cerebrospinalis and urine.

12. The method of claim 1, wherein the label is selected from the group consisting of a radioactive label, an enzyme label, a fluorescent label, a chemiluminescent label, an electrochemiluminescent label and a dyed particle.

13. The method of claim 1, wherein the substance to be detected is an antigen and the capture reagent is an antibody or antibody fragment.

14. The method of claim 1, wherein the substance to be detected is an antibody and the capture reagent is an antigen or hapten.

15. The method of claim 1, wherein the substance to be detected is a nucleic acid and the capture reagent is selected from the group consisting of a nucleic acid oligomer, a nucleic acid polymer and a nucleic acid analogue.

16. The method of claim 15, wherein the capture reagent is a nucleic acid analogue, wherein the nucleic acid analogue is a peptidic nucleic acid.

17. The method of claim 1, wherein the detection reagent specifically binds to the substance to be detected.

18. The method of claim 17, wherein the substance to be detected is an antigen and the detection reagent is an antibody or antibody fragment.

19. The method of claim 17, wherein the substance to be detected is an antibody and the detection reagent is selected from the group consisting of an antigen, hapten, antibody and antibody fragment.

20. The method of claim 17, wherein the substance to be detected is a nucleic acid and the detection reagent is selected from the group consisting of a nucleic acid oligomer, a nucleic acid polymer and a nucleic acid analogue.

21. The method of claim 20, wherein the detection reagent is a nucleic acid analogue, wherein the nucleic acid analogue is a peptidic nucleic acid.

22. The method of claim 1, wherein step (b)(1)(i) is performed, and the labelled detection reagent is bound after the at least a portion of the amount of the substance to be detected is bound.

23. The method of claim 1, wherein the detection reagent is specific for the capture reagent, and the detection reagent and the substance to be detected compete for binding to the capture reagent.

24. The method of claim 23, wherein the substance to be detected is an antigen and the detection reagent is an antibody or antibody fragment.

25. The method of claim 23, wherein the substance to be detected is an antibody and the detection reagent is selected from the group consisting of an antigen, hapten, antibody and antibody fragment.

26. The method of claim 23, wherein the substance to be detected is a nucleic acid and the detection reagent is selected from the group consisting of a nucleic acid oligomer, a nucleic acid polymer and a nucleic acid analogue.

27. The method of claim 26, wherein the detection reagent is a nucleic acid analogue, wherein the nucleic acid analogue is a peptidic nucleic acid.

28. The method of claim 1, wherein, in step (b), the test sample is simultaneously incubated with the first solid phase and the second solid phase, and is thereafter incubated with the capture reagent.

29. The method of claim 1, wherein, in step (b), the test sample is simultaneously incubated with the first solid phase, the second solid phase and the capture reagent.

30. A method for the qualitative or quantitative detection of a substance to be detected in a test sample, the method comprising:
   (a) providing an immunoassay or nucleic acid hybridization assay comprising
      (1) a first solid phase;
      (2) an amount of a capture reagent having a first binding site and a second binding site; and
      (3) a second solid phase which does not specifically bind the capture reagent via the first binding site, wherein avidin or streptavidin is bound to the second solid phase and the second solid phase is saturated with biotin or a biotin derivative so that the second solid phase does not specifically bind the capture reagent, or the avidin or streptavidin binding site is modified so that the avidin or streptavidin does not specifically bind biotin or a biotin derivative;
   (b) incubating the test sample, containing an amount of the substance to be detected therein, with the immunoassay or nucleic hybridization assay to
      (1) directly or indirectly specifically bind at least a portion of the amount of the substance to be detected to either
         (i) the first solid phase via the second binding site of the capture reagent, wherein the capture reagent directly or indirectly specifically binds to the first solid phase via the first binding site, and binding a labelled detection reagent either to at least a portion of the amount of the substance to be detected or at least a portion of the amount of the capture reagent, and thereafter qualitatively or quantitatively detecting the label as an indication of the presence or the amount of the substance to be detected, or
         (ii) a labelled detection reagent, and thereafter qualitatively or quantitatively detecting the label as an indication of the presence or the amount of the substance to be detected, and
      (2) unspecifically bind interfering substances to the second solid phase.

31. The method of claim 30, wherein the avidin or steptavidin is bound to the first solid phase via thermo-bovine-serum-albumin.

32. The method of claim 30, wherein the avidin or streptavidin binding site is modified by covalently binding a compound to the binding site.

33. The method of claim 32, wherein the compound is biotin.

34. A method for the qualitative or quantitative detection of a substance to be detected in a test sample, the method comprising:
   (a) providing an immunoassay or nucleic acid hybridization assay comprising
      (1) a first solid phase;
      (2) an amount of a capture reagent having a first binding site and a second binding site; and
      (3) a second solid phase which is does not specifically bind the capture reagent via the first binding site, wherein avidin or streptavidin is bound to the second solid phase and the avidin or streptavidin binding site is modified by covalently binding to the binding site a biotin-containing compound which is subsequently photoactivated, so that the avidin or streptavidin does not specifically bind biotin or a biotin derivative;
   (b) incubating the test sample, containing an amount of the substance to be detected therein, with the immunoassay or nucleic hybridization assay to
      (1) directly or indirectly specifically bind at least a portion of the amount of the substance to be detected to either
         (i) the first solid phase via the second binding site of the capture reagent, wherein the capture reagent directly or indirectly specifically binds to the first solid phase via the first binding site, and binding a labelled detection reagent either to at least a portion of the amount of the substance to be detected or at least a portion of the amount of the capture reagent, and thereafter qualitatively or quantitatively detecting the label as an indication of the presence or the amount of the substance to be detected, or
         (ii) a labelled detection reagent, and thereafter qualitatively or quantitatively detecting the label as an indication of the presence or the amount of the substance to be detected, and
      (2) unspecifically bind interfering substances to the second solid phase.

35. The method of claim 34, wherein the biotin-containing compound is biotin-DADOO-AB.

36. A method for the qualitative or quantitative detection of a substance to be detected in a test sample, the method comprising:
   (a) providing an immunoassay or nucleic acid hybridization assay comprising
      (1) a first solid phase;
      (2) an amount of a capture reagent having a first binding site and a second binding site; and
      (3) a second solid phase which does not specifically bind the capture reagent via the first binding site, wherein avidin or streptavidin is bound to the second solid phase and the avidin or streptavidin binding site is modified by derivatizing at least one amino acid of the binding site, so that the avidin or streptavidin does not specifically bind biotin or a biotin derivative;
   (b) incubating the test sample, containing an amount of the substance to be detected therein, with the immunoassay or nucleic hybridization assay to
      (1) directly or indirectly specifically bind at least a portion of the amount of the substance to be detected to either
         (i) the first solid phase via the second binding site of the capture reagent, wherein the capture reagent directly or indirectly specifically binds to the first solid phase via the first binding site, and binding a labelled detection reagent either to at least a portion of the amount of the substance to be detected or at least a portion of the amount of the capture reagent, and thereafter qualitatively or quantitatively detecting the label as an indication of the presence or the amount of the substance to be detected, or
         (ii) a labelled detection reagent, and thereafter qualitatively or quantitatively detecting the label as an indication of the presence or the amount of the substance to be detected, and
      (2) unspecifically bind interfering substances to the second solid phase.

37. A method for the qualitative or quantitative detection of a substance to be detected in a test sample, the method comprising:

(a) providing an immunoassay or nucleic acid hybridization assay comprising
  (1) a first solid phase;
  (2) an amount of a capture reagent having a first binding site and a second binding site; and
  (3) a second solid phase which is does not specifically bind the capture reagent via the first binding site, wherein avidin or streptavidin is bound to the second solid phase and the avidin or streptavidin binding site is modified by substituting, deleting or inserting at least one amino acid by genetic engineering, so that the avidin or streptavidin does not specifically bind biotin or a biotin derivative;
(b) incubating the test sample, containing an amount of the substance to be detected therein, with the immunoassay or nucleic hybridization assay to
  (1) directly or indirectly specifically bind at least a portion of the amount of the substance to be detected to either
    (i) the first solid phase via the second binding site of the capture reagent, wherein the capture reagent directly or indirectly specifically binds to the first solid phase via the first binding site, and binding a labelled detection reagent either to at least a portion of the amount of the substance to be detected or at least a portion of the amount of the capture reagent, and thereafter qualitatively or quantitatively detecting the label as an indication of the presence or the amount of the substance to be detected, or
    (ii) a labelled detection reagent, and thereafter qualitatively or quantitatively detecting the label as an indication of the presence or the amount of the substance to be detected, and
  (2) unspecifically bind interfering substances to the second solid phase.

* * * * *